US006458757B1

United States Patent
Storet

(10) Patent No.: US 6,458,757 B1
(45) Date of Patent: Oct. 1, 2002

(54) METHOD FOR PREPARING SCENTING COMPOSITIONS AND SCENTED PRODUCTS, AND RESULTING PRODUCTS

(75) Inventor: Isabelle Storet, Les Eparres (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/051,666

(22) PCT Filed: Oct. 25, 1996

(86) PCT No.: PCT/FR96/01673

§ 371 (c)(1),
(2), (4) Date: Apr. 24, 1998

(87) PCT Pub. No.: WO97/15547

PCT Pub. Date: May 1, 1997

(30) Foreign Application Priority Data

Oct. 27, 1995 (FR) .............................. 95 12687

(51) Int. Cl.$^7$ ..................................... A61K 7/46
(52) U.S. Cl. ....................... 512/21; 512/20; 512/25; 560/55; 560/64; 560/66; 560/103; 424/69; 424/76.4; 510/102; 510/107
(58) Field of Search .................. 512/20, 21, 25; 560/103, 55, 64, 66; 424/69, 76.4; 510/102, 107

(56) References Cited

U.S. PATENT DOCUMENTS 3,076,017 A * 1/1963 Grisley, Jr. et al. ........... 560/75
3,457,286 A * 7/1969 Dexter et al. ................. 560/63
3,714,227 A * 1/1973 Ueno et al. .................... 560/67
3,954,839 A * 5/1976 Dexter et al. ................. 560/75
4,276,431 A * 6/1981 Schnegg et al. .............. 560/67
4,293,544 A * 10/1981 Elmi .............................. 424/60
4,387,047 A * 6/1983 Sundt et al. ................. 426/534
4,624,802 A * 11/1986 Schaper et al. ......... 252/522 R
5,360,924 A * 11/1994 Beller et al. .................. 560/55
5,525,247 A * 6/1996 Miyaji et al. ................. 252/18

FOREIGN PATENT DOCUMENTS

JP        08104666      *   4/1996

OTHER PUBLICATIONS

Journal of Organic Chemistry, vol. 54, No. 1 Jan. 1989, EASTON US, pp. 38–46.*

* cited by examiner

*Primary Examiner*—Jill Warden
*Assistant Examiner*—Monique T. Cole

(57) ABSTRACT

The present invention relates to a process for the production of perfuming compositions, to perfumed products, and to products obtained therefrom. More specifically, the present invention concerns a process for the production of perfuming compositions, perfumed products and substances for perfumery characterized in that they comprise, as an active ingredient with an influence on the scent, an effective quantity of an alkylsalicylic acid ester.

24 Claims, No Drawings

METHOD FOR PREPARING SCENTING COMPOSITIONS AND SCENTED PRODUCTS, AND RESULTING PRODUCTS

This application is an application under 35 U.S.C. Section 371 of International Application Number PCT/FR96/01673, filed Oct. 25, 1996.

The present invention relates to a process for the production of perfuming compositions, to perfumed products, and to products so obtained.

In particular, the present invention envisages their use in the perfumery field. The compounds exhibit very interesting olfactory properties and can be used, inter alia, to prepare perfuming compositions and perfumed products.

The perfumery industry is constantly seeking products which by their originality, volume and the strength of their fragrance can endow compositions containing them with a unique character.

We have now discovered that alkylsalicylic acid esters as defined below, in particular methylsalicylic acid esters, exhibit novel olfactory properties.

It should be noted that it is impossible for the skilled person to predict whether a given chemical compound will or will not have an interesting scent from the olfactory viewpoint which could be used in the perfumery field.

More specifically, the present invention concerns a process for the production of perfuming compositions, perfumed products and substances for perfumery characterized in that an effective quantity of an alkylsalicylic acid ester is added to the usual constituents of these compositions, substances and finished products.

The present invention also concerns perfuming compositions, perfumed substances and products characterized in that they comprise, as an active ingredient having an influence on the scent, an effective quantity of an alkylsalicylic acid ester.

The invention thus resides in a novel use of esters of an alkylsalicylic acid as a perfuming ingredient.

The invention also relates to certain alkylsalicylic acid esters as novel products.

The perfuming ingredient of the invention is an alkylsalicylic acid ester. More particularly, it has the following general formula (I):

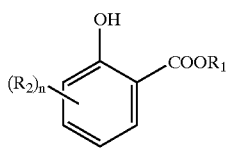
(I)

in which formula (I):
n is a number equal to 1 or 2.
$R_1$ represents a hydrocarbon radical which may or may not be substituted, containing 1 to 40 carbon atoms, more particularly a linear or branched, saturated or unsaturated, aliphatic, acyclic radical, or a saturated or unsaturated, monocyclic or polycyclic, carbocyclic or heterocyclic radical;
$R_2$ represents an aliphatic radical, preferably saturated, preferably less than 4.

More particularly, the alkylsalicylic acid esters have formula (I) in which the different radicals $R_1$ and $R_2$ have the following meaning.

The number of carbon atoms in $R_1$ is generally between 1 and 40 carbon atoms, preferably between 1 and 12 carbon atoms.

Radical $R_1$ can be a monovalent radical which may or may not be substituted, which may be a linear or branched, saturated or unsaturated, aliphatic acyclic radical; or a saturated or unsaturated, monocyclic or polycyclic, carbocyclic or heterocyclic radical.

Radical $R_1$ is a linear or branched, saturated or unsaturated, aliphatic acyclic radical.

More precisely, $R_1$ is a linear or branched alkyl, alkenyl or alkadienyl radical preferably containing 1 to 40 carbon atoms.

The hydrocarbon chain can optionally be interrupted by a heteroatom (for example oxygen or sulphur) or by one of the following groups: —CO—, —COO—, and/or can carry one of the following substituents: —OH, —COOR$_3$, —, —CF$_3$: in these formulae, $R_3$ preferably represents hydrogen or a linear or branched alkyl radical containing 1 to 4 carbon atoms, more particularly a methyl or ethyl radical.

$R_1$ can represent a carbocyclic monocyclic radical. The number of carbon atoms in the cycle can vary from 3 to 8 carbon atoms, but is preferably 5 or 6 carbon atoms.

The carbocycle can be saturated or can contain 1 or 2 unsaturated bonds in the cycle, preferably 1 or 2 double bonds.

Examples of carbocycles area cycloalkoyl or cycloalkenyl radical containing 3 to 8 carbon atoms, preferably a cyclohexyl, cyclohexen-yl or cyclohepten-yl radical.

When $R_1$ represents a saturated or unsaturated carbocyclic monocyclic radical, it is possible for one or more carbon atoms of the cycle to be replaced by one or more heteroatoms, preferably oxygen, nitrogen or sulphur or by a functional group, preferably a carbonyl or ester group, resulting in a heterocyclic monocyclic compound. The number of atoms in the cycle can vary from 3 to 8 atoms but is preferably 5 or 6 atoms.

Radical $R_1$ can also be carbocyclic and polycyclic, preferably bicyclic which means that at least two cycles have two carbon atoms in common. For polycyclic radicals, the number of carbon atoms in each cycle is between 3 and 6: the total number of carbon atoms is preferably 7.

Examples of currently encountered bicyclic structures are given below:

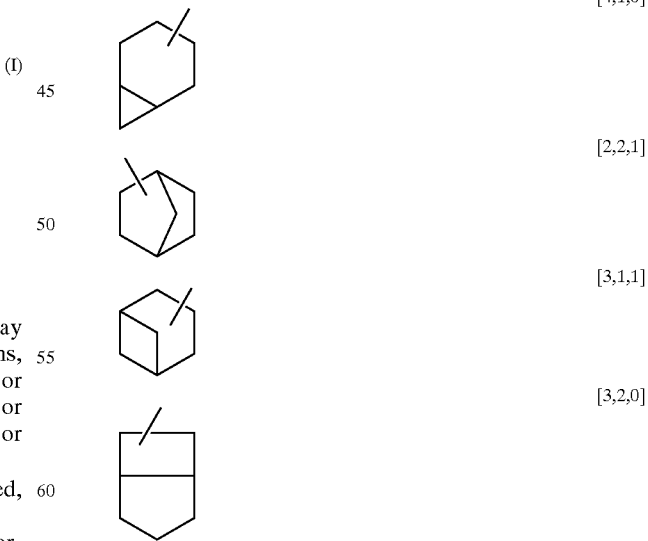

Radical $R_1$ can also be heterocyclic and polycyclic, preferably bicyclic, meaning that at least two cycles have two atoms in common. In this case, the number of atoms in each cycle is between 3 and 6, more preferably 5 or 6.

Radical $R_1$ can represent a linear or branched, saturated or unsaturated aliphatic radical carrying a cyclic substituent. Examples of cyclic substituents are cycloaliphatic, aromatic or heterocyclic substituents, in particular cycloaliphatic compounds containing 6 carbon atoms in the cycle, or benzene rings. More particular examples are arylalkyl radicals containing 6 to 12 carbon atoms, preferably the benzyl radical.

It should be noted that if radical $R_1$ contains a cycle, it is possible for the cycle to carry a substituent of any type. The substituents usually carried by the cycle are one or more alkyl or alkoxy radicals preferably containing 1 to 4 carbon atoms, preferably three methyl radicals, a methylene radical (corresponding to an exocyclic bond), an alkenyl radical, preferably an isopropen-yl radical, or a halogen atom, preferably chlorine or bromine.

More preferably, the alkylsalicylic acid esters have the following general formula (Ia):

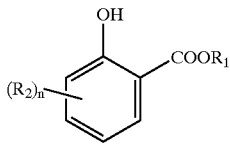

(Ia)

in which formula (Ia):

n is a number equal to 1 or 2;

$R_1$ represents a linear or branched alkyl radical containing 1 to 12 carbon atoms, preferably 1 to 8: or a cycloalkyl radical preferably containing 6 carbon atoms, or an aralkyl radical containing 6 to 12 carbon atoms, preferably 7 or 8 carbon atoms;

$R_2$ represents a linear or branched alkyl radical containing 1 to 4 carbon atoms, preferably 1 or 2.

Of compounds with formula (I), those in which radical $R_1$ contains more than two carbon atoms are novel products and are claimed as such.

Preferred compounds are those with formula (Ia) in which $R_1$ represents an alkyl radical such as methyl, ethyl, n-propyl, isopropyl, butyl, isobutyl, sec-butyl, tert-butyl, amyl, isoamyl, n-hexyl, 2-ethylhexyl; a cyclohexyl radical; or a benzyl radical or a β-phenylethyl radical, and $R_2$ represents a methyl or ethyl radical.

Specific examples of alkylsalicylic acid esters with formula (I) are, among others:

methyl 2-hydroxy-3-methyl-benzoate;
ethyl 2-hydroxy-3-methyl-benzoate;
isopropyl 2-hydroxy-3-methyl-benzoate;
n-propyl 2-hydroxy-3-methyl-benzoate;
n-butyl 2-hydroxy-3-methyl-benzoate;
isobutyl 2-hydroxy-3-methyl-benzoate;
amyl 2-hydroxy-3-methyl-benzoate;
isoamyl 2-hydroxy-3-methyl-benzoate;
n-hexyl 2-hydroxy-3-methyl-benzoate;
2-ethylhexyl 2-hydroxy -3-methyl-benzoate;
cyclohexyl 2-hydroxy-3-methyl-benzoate;
benzyl 2-hydroxy-3-methyl-benzoate;
β-phenylethyl 2-hydroxy-3-methyl-benzoate;
methyl 2-hydroxy-4-methyl-benzoate;
ethyl 2-hydroxy-4-methyl-benzoate;
isopropyl 2-hydroxy-4-methyl-benzoate;
n-propyl 2-hydroxy-4-methyl-benzoate;
n-butyl 2-hydroxy-4-methyl-benzoate;
isobutyl 2-hydroxy-4-methyl-benzoate;
amyl 2-hydroxy-4-methyl-benzoate;
isoamyl 2-hydroxy-4-methyl-benzoate;
n-hexyl 2-hydroxy-4-methyl-benzoate;
2-ethylhexyl 2-hydroxy-4-methyl-benzoate;
cyclohexyl 2-hydroxy-4-methyl-benzoate;
benzyl 2-hydroxy-4-methyl-benzoate;
β-phenylethyl 2-hydroxy-4-methyl-benzoate;
methyl 2-hydroxy-5-methyl-benzoate;
ethyl 2-hydroxy-5-methyl-benzoate;
isopropyl 2-hydroxy-5-methyl-benzoate;
n-propyl 2-hydroxy-5-methyl-benzoate;
n-butyl 2-hydroxy-5-methyl-benzoate;
isobutyl 2-hydroxy-5-methyl-benzoate;
amyl 2-hydroxy-5-methyl-benzoate;
isoamyl 2-hydroxy-5-methyl-benzoate;
n-hexyl 2-hydroxy-5-methyl-benzoate;
2-ethylhexyl 2-hydroxy-5-methyl-benzoate;
cyclohexyl 2-hydroxy-5-methyl-benzoate:
benzyl 2-hydroxy-5-methyl-benzoate;
β-phenylethyl 2-hydroxy-5-methyl-benzoate Compounds with formula (I) give off a very interesting scent.

These products can be used as perfuming ingredients in perfuming compositions, substances and perfumed products.

The term "perfuming compositions" means mixtures of various ingredients such as solvents, solid or liquid supports, fixatives, various scenting compounds, into which alkylsalicylic acid esters preferably with formula (I) are incorporated, which are used to produce a variety of types of finished products, with the desired fragrance.

Perfume bases constitute preferred examples of perfuming compositions in which the alkylsalicylic acid esters preferably with formula (I) can advantageously be used.

Eau de toilette, after-shave lotion, perfume, soap, bath or shower gel or deodorant or antiperspirant in the form of sticks or lotions constitute examples of finished products or substances which the alkylsalicylic acid esters preferably with formula (I) endow with their original note.

They can also be used in all types of shampoos and hair-care products.

They can also perfume all types of talcs or powders.

They can also be used in room sprays or any cleaning product.

A further example of compositions in which the compounds can advantageously be used is represented by the usual detergent compositions. Such compositions generally comprise one or more of the following ingredients: anionic, cationic or amphoteric surfactants, bleaching agents, optical brighteners, various fillers, and anti-redepositing agents. The nature of these various components is not critical and the alkylsalicylic acid esters, preferably with formula (I) can be added to any type of detergent composition. They can be introduced into fabric softeners, in liquid form or into compositions deposited on a support, usually a non-woven support, for use in clothes dryers.

The amount of the compositions of the invention of alkylsalicylic acid ester, preferably with formula (I), expressed as the percentage by weight in the composition under consideration, depends on the nature of the composition (a base for a perfume or eau de toilette, for example) and the strength and nature of the desired influence in the finished product. It is clear that in a perfume base the quantity of alkylsalicylic acid ester preferably with formula (I) can be very high, for example over 50% by weight, and can attain 90% by weight while in a perfume, an eau de toilette or an after-shave lotion, this quantity can be below 50% by weight.

In detergent compositions, in particular for domestic use, and in soaps, the quantity of alkylsalicylic acid ester can be of the order of 1% to 2%.

It can also be used in perfumed shampoos in an amount of 0.5% to 2%, or to perfume any hair product.

Thus the lower limit of the amount of alkylsalicylic ester preferably with formula (I) can be that which causes a perceptible modification in the scent or fragrance or the note of the finished product. In some cases, this minimum amount can be of the order of 0.01% by weight. Clearly, quantities which are not included in the limits indicated above can be employed without departing from the scope of the invention.

One route to alkylsalicylic esters consists of reacting an alkylsalicylic acid and an alcohol in the presence of an acid catalyst.

More particularly, the following are reacted:
an alkylsalicylic acid with formula (II):

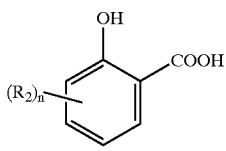

(II)

where $R_2$ and nitrogen have the meanings given above, an alcohol with formula (III):

$R_1$—OH                                                (III)

where $R_1$ has the meaning given above.

Particular examples of compounds with formula (II) are 2-hydroxy-3-methyl-benzoic acid, 2-hydroxy-4-methyl-benzoic acid, and 2-hydroxy-5-methyl-benzoic acid.

Preferred examples of alcohols with formula (III) are primary or secondary alcohols containing 1 to 12 carbon atoms, preferably methanol, ethanol, cyclohexanol, benzyl alcohol, and β-phenylethyl alcohol.

In the process of the invention, the acid is reacted with an alcohol with formula (III).

Compounds with formula (II) are commercially available.

A number of preparation modes can be envisaged.

A first variation consists of reacting an alkylsalicylic acid with an alcohol with formula (III).

It is also possible to carry out esterification in the presence of an organic solvent. The organic solvent is selected so that it forms an azeotrope with water and the boiling point of the azeotrope with water is lower than that of the alcohol used. Examples of solvents are toluene, cumene and pseudocumene.

It is preferable to use a direct esterification process carried out in the absence of an organic solvent for alcohols containing 1 to 5 carbon atoms.

In the case of heavy alcohols containing more than 5 carbon atoms, it is preferable to carry out the reaction in the presence of an organic solvent The different reactions are carried out in the presence of a conventional acid type catalyst. Particular examples are sulphuric acid, hydrochloric acid, p-toluene sulphonic acid, alkoyl titanates, preferably isopropyl or n-butyl titanates, and antimony oxide.

The quantity of reactants present is determined so that the alcohol with formula (III) is generally in excess with respect to the alkylsalicylic acid. The excess varies widely, preferably from 50% to 3000% with respect to the stoichiometric quantity. More preferably, it is selected to be between 100% and 2000% of the stoichiometric quantity.

The quantity of catalyst used, expressed with respect to the weight of alkylsalicylic acid, is advantageously between 1% and 30%.

When an organic solvent is present, the quantity used can vary widely. As an indication, the quantity of organic solvent can represent 50% to 1000% of the weight of the alkylsalicylic acid used.

The reaction temperature is selected so that it is sufficient to allow the reaction to occur.

The reaction temperature is preferably 50° C. to 150° C.

The reaction is advantageously carried out at atmospheric pressure.

The reaction is preferably carried out in an inert gas atmosphere which can be nitrogen or a rare gas, preferably argon.

From a practical viewpoint, the process of the invention is simple to carry out.

The different reactants can be introduced in any order. The order of introducing the reactants is preferably as follows: the alkylsalicylic acid and alcohol with formula (III) are introduced, then the acid catalyst.

The reaction medium is heated to the desired temperature, while stirring the reaction medium.

During the reaction, water forms in the reaction medium. In a preferred variation of the invention, the water is eliminated from the reaction medium as it is formed using any known means, in particular azeotropic distillation.

At the end of the reaction, the desired alkylsalicylic acid ester is obtained, along with excess alcohol with formula (III) and the catalyst.

The alkylsalicylic acid ester can be recovered from the reaction medium using any suitable means.

Thus it can be washed with water followed by neutralisation with a base.

The quantity of base, preferably sodium hydroxide, carbonate or bicarbonate, is such that the pH is in the range 6 to 8.

The organic phase is separated out and fractionated by distillation. Usually, the excess alcohol with formula (III) is recovered first then the alkylsalicylic acid ester, preferably with formula (I).

Examples of implementations of the invention will now be given.

EXAMPLE 1

1. In this example, ethyl 2-hydroxy 4-methyl-benzoate was produced.

50 g of 2-hydroxy-4-methyl-benzoic acid was added to 250 ml of ethanol in a reactor. 40 ml of sulphuric acid was introduced dropwise using a dropping funnel; it was cooled if the alcohol boiled.

It was heated to reflux for 3 hours, with stirring.

After cooling to room temperature, it was poured onto about 100 ml of ice water. and the alcohol was evaporated off under reduced pressure.

The aqueous phase was extracted three times using ethyl ether.

The combined organic phases were washed with a saturated solution of sodium bicarbonate to a neutral pH, then washed once with water to eliminate the salts.

The organic phase was dried over magnesium sulphate and evaporated under reduced pressure (200 mm of mercury/$2.66 \times 10^4$ Pa) to obtain the crude ester.

The ethyl ester was distilled at 82° C. under a reduced pressure of 1 mm of mercury (133 Pa), to produce ethyl 2-hydroxy-4-methyl-benzoate with a purity of over 97%.

The ethyl 2-hydroxy-4-methyl-benzoate had a sensual flowery scent typical of Ylang notes.

EXAMPLE 2

1. In this example, n-hexyl 2-hydroxy-4-methyl-benzoate was produced.

59 g of 2-hydroxy-4-methyl-benzoic acid and 41 g of dry n-hexanol were added to 150 ml of toluene in a Dean-Stark condenser. Finally, 5% of p-toluene sulphonic acid was added, which acted as an acid catalyst.

It was refluxed for 24 hours during which water could be seen to be eliminated.

It was cooled to ambient temperature and the organic phase was washed to a neutral pH with a saturated solution of sodium bicarbonate.

The organic phase was washed with water before drying over magnesium sulphate. The toluene and a portion of the n-hexanol were evaporated off under reduced pressure.

The crude ester was distilled under reduced pressure of 2 mm of mercury (2.66 Pa) to produce n-hexyl 2-hydroxy-4-methyl-benzoate in a purity of over 97%.

2. The n-hexyl 2-hydroxy-4-methyl-benzoate had a terpenic plum-tree evernia scent.

EXAMPLE 3

1. In this example, isopropyl 2-hydroxy-4-methyl-benzoate was produced.

Gaseous hydrochloric acid was bubbled into 250 ml of dry isopropanol in a reactor until a 2% by weight HCl solution was obtained.

25 g of 2-hydroxy-4-methyl-benzoic acid was then added and it was heated under reflux for 24 hours.

The alcohol was evaporated off and the residue was taken up in a saturated aqueous solution of sodium bicarbonate.

The aqueous phase was extracted three times with ethyl ether.

The combined organic phases were washed with water, dried over magnesium sulphate then evaporated off.

The crude ester was distilled under reduced pressure of 2 mm of mercury (2.66 Pa).

2. The isopropyl 2-hydroxy-4-methyl-benzoate had a celery scent.

EXAMPLE 4

1. In this example, methyl 2-hydroxy-4-methyl-benzoate was produced using the method described in Example 1.

2. The methyl 2-hydroxy-4-methyl-benzoate had a phenolic aniseed scent.

EXAMPLE 5

1. In this example, isoamyl 2-hydroxy 4-methyl-benzoate was produced using the method described in Example 3.

2. The isoamyl 2-hydroxy 4-methyl-benzoate had a fruity leather scent.

EXAMPLE 6

1. In this example, methyl 2-hydroxy-3-methyl-benzoate was produced using the method described in Example 1.

2. The methyl 2-hydroxy-3-methyl-benzoate had a leathery scent.

EXAMPLE 7

1. In this example, isoamyl 2-hydroxy-3-methyl-benzoate was produced using the method described in Example 3.

2. The isoamyl 2-hydroxy-3-methyl-benzoate had a fruity leather scent.

EXAMPLE 8

1. In this example, n-hexyl 2-hydroxy-3-methyl-benzoate was produced using the method described in Example 2.

2. The n-hexyl 2-hydroxy-3-methyl-benzoate had a fruity scent.

EXAMPLE 9

1. In this example, isopropyl 2-hydroxy-3-methyl-benzoate was produced using the method described in Example 3.

2. The isopropyl 2-hydroxy-3-methyl-benzoate had a leathery scent.

EXAMPLE 10

1. In this example, ethyl 2-hydroxy-3-methyl-benzoate was produced using the method described in Example 1.

2. The ethyl 2-hydroxy-3-methyl-benzoate had a leathery scent.

EXAMPLE 11

1. In this example, methyl 2-hydroxy-5-methyl-benzoate was produced using the method described in Example 1.

2. The methyl 2-hydroxy-5-methyl-benzoate had a saffron violet scent.

EXAMPLE 12

1. In this example, ethyl 2-hydroxy-5-methyl-benzoate was produced using the method described in Example 1.

2. The ethyl 2-hydroxy-5-methyl-benzoate had a may-blossom scent.

EXAMPLE 13

1. In this example, propyl 2-hydroxy-5-methyl-benzoate was produced using the method described in Example 1.

2. The propyl 2-hydroxy-5-methyl-benzoate had a may-blossom scent.

EXAMPLE 14

1. In this example, butyl 2-hydroxy-5-methyl-benzoate was produced using the method described in Example 1.

2. The butyl 2-hydroxy-5-methyl-benzoate had a may-blossom scent.

EXAMPLE 15

1. In this example, amyl 2-hydroxy-5-methyl-benzoate was produced using the method described in Example 1.

2. The amyl 2-hydroxy-5-methyl-benzoate had a may-blossom scent.

EXAMPLE 16

1. In this example, n-hexyl 2-hydroxy-5-methyl-benzoate was produced using the method described in Example 2.

2. The n-hexyl 2-hydroxy-5-methyl-benzoate had a may-blossom scent.

EXAMPLE 17

1. In this example, benzyl 2-hydroxy-5-methyl-benzoate was produced using the method described in Example 2.

2. The benzyl 2-hydroxy-5-methyl-benzoate had a may-blossom scent.

EXAMPLE 18

1. in this example, cyclohexyl 2-hydroxy-5-methyl-benzoate was produced using the method described in Example 3.

2. The cyclohexyl 2-hydroxy-5-methyl-benzoate had a may-blossom scent.

EXAMPLE 19

1. In this example, isopropyl 2-hydroxy-5-methyl-benzoate was produced using the method described in Example 3.

2. The isopropyl 2-hydroxy-5-methyl-benzoate had a may-blossom scent.

EXAMPLE 20

1. In this example, isobutyl 2-hydroxy-5-methyl-benzoate was produced using the method described in Example 3.

2. The isobutyl 2-hydroxy-5-methyl-benzoate had a may-blossom scent.

EXAMPLE 21

1. In this example, isoamyl 2-hydroxy-5-methyl-benzoate was produced using the method described in Example 3.

2. The isoamyl 2-hydroxy-5-methyl-benzoate had a may-blossom scent.

EXAMPLE 22

This is an example of the use of ethyl 2-hydroxy 4-methyl-benzoate in a perfuming composition in liquid form:
10% of ethyl 2-hydroxy-4-methyl-benzoate;
10% of benzyl salicylate;
10% of hydroxycitronellal;
10% of methyl anthranilate;
2% of isoeugenol;
4% of gamma nonalactone;
54% of alpha hexylcinnamic aldehyde.

What is claimed is:

1. A process for the production of a perfuming composition, a perfumed product or a substance for perfumery, comprising the step of adding an effective perfuming amount of an alkylsalicylic acid ester to said composition, substance and finished product, wherein the alkylsalicylic acid ester has general formula (I):

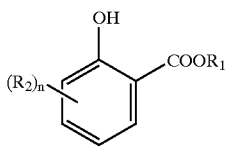

(I)

wherein:

n is a number equal to 1 or 2;

$R_1$ represents a hydrocarbon radical, containing 1 to 40 carbon atoms; or a saturated or unsaturated, monocyclic or polycyclic, carbocyclic or heterocyclic radical; and $R_2$ represents an aliphatic optionally saturated radical having 1 to 4 carbon atoms.

2. A process according to claim 1, wherein:

$R_1$ represents a linear or branched, saturated or unsaturated, aliphatic, acyclic radical; and $R_2$ represents an aliphatic saturated radical with less than 4 carbon atoms.

3. A process according to claim 1, wherein the alkylsalicylic acid ester has general formula (Ia):

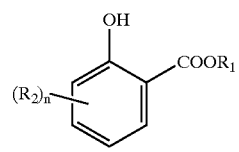

(Ia)

wherein:

n is a number equal to 1 or 2;

$R_1$ represents a linear or branched alkyl radical containing 1 to 12 carbon atoms; a cycloalkyl radical, or an aralkyl radical containing 6 to 12 carbon atoms;

$R_2$ represents a linear or branched alkyl radical containing 1 to 4 carbon atoms.

4. A process according to claim 3, wherein $R_1$ represents a linear or branched alkyl radical containing 1 to 8 carbon atoms;

a cycloalkyl radical containing 6 carbon atoms, or an aralkyl radical containing 7 or 8 carbon atoms;

$R_2$ represents a linear or branched alkyl radical containing 1 to 2 carbon atoms.

5. A process according to claim 1, wherein the alkylsalicylic ester has general formula (I), wherein $R_1$ is methyl, ethyl, n-propyl, isopropyl, butyl, isobutyl, sec-butyl, tert-butyl, amyl, isoamyl, n-hexyl 2-ethylhexyl, a cyclohexyl radical; a benzyl radical; or a β-phenylethyl radical, and $R_2$ is methyl or ethyl radical.

6. A process according to claim 1, wherein the alkylsalicylic acid ester is:
methyl 2-hydroxy-3-methyl-benzoate;
ethyl 2-hydroxy-3-methyl-benzoate;
isopropyl 2-hydroxy-3-methyl-benzoate;
n-propyl 2-hydroxy-3-methyl-benzoate;
n-butyl 2-hydroxy-3-methyl-benzoate;
isobutyl 2-hydroxy-3-methyl-benzoate;
amyl 2-hydroxy-3-methyl-benzoate;
isoamyl 2-hydroxy-3-methyl-benzoate;
n-hexyl 2-hydroxy-3-methyl-benzoate;
2-ethylhexyl 2-hydroxy-3-methyl-benzoate;
cyclohexyl 2-hydroxy-3-methyl-benzoate;
benzyl 2-hydroxy-3-methyl-benzoate;
β-phenylethyl 2-hydroxy-3-methyl-benzoate;
methyl 2-hydroxy-4-methyl-benzoate;
ethyl 2-hydroxy-4-methyl-benzoate;
isopropyl 2-hydroxy-4-methyl-benzoate;
n-propyl 2-hydroxy-4-methyl-benzoate;
n-butyl 2-hydroxy-4-methyl-benzoate;
isobutyl 2-hydroxy-4-methyl-benzoate;
amyl 2-hydroxy-4-methyl-benzoate;
isoamyl 2-hydroxy-4-methyl-benzoate;
n-hexyl 2-hydroxy-4-methyl-benzoate;
2-ethylhexyl 2-hydroxy-4-methyl-benzoate;
cyclohexyl 2-hydroxy-4-methyl-benzoate;
benzyl 2-hydroxy-4-methyl-benzoate;
β-phenylethyl 2-hydroxy-4-methyl-benzoate;
methyl 2-hydroxy-5-methyl-benzoate;
ethyl 2-hydroxy-5-methyl-benzoate;

isopropyl 2-hydroxy-5-methyl-benzoate;
n-propyl 2-hydroxy-5-methyl-benzoate;
n-butyl 2-hydroxy-5-methyl-benzoate;
isobutyl 2-hydroxy-5-methyl-benzoate;
amyl 2-hydroxy-5-methyl-benzoate;
isoamyl 2-hydroxy-5-methyl-benzoate;
n-hexyl 2-hydroxy-5-methyl-benzoate;
2-ethylhexyl 2-hydroxy-5-methyl-benzoate;
cyclohexyl 2-hydroxy-5-methyl-benzoate;
benzyl 2-hydroxy-5-methyl-benzoate; or
β-phenylethyl 2-hydroxy-5-methyl-benzoate.

7. A perfuming composition, a perfumed substance, comprising an effective perfuming amount of an ester of an alkylsalicylic acid, wherein the alkylsalicylic acid ester has general formula (I):

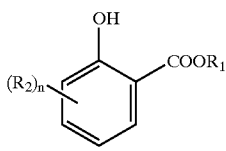

(I)

wherein:
   n is a number equal to 1 or 2;
   $R_1$ represents a hydrocarbon radical, containing 1 to 40 carbon atoms; or a saturated or unsaturated, monocyclic or polycyclic, carbocyclic or heterocyclic radical; and
   $R_2$ represents an aliphatic optionally saturated radical having 1 to 4 carbon atoms.

8. A composition according to claim 7, wherein $R_1$ represents a linear or branched, saturated or unsaturated, aliphatic, acyclic radical; and
   $R_2$ represents an aliphatic saturated radical with less than 4 carbon atoms.

9. Compositions according to claim 7, wherein the alkylsalicylic acid ester has general formula (Ia):

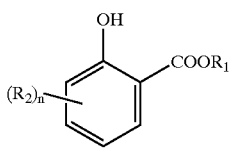

(Ia)

wherein:
   n is a number equal to 1 or 2;
   $R_1$ represents a linear or branched alkyl radical containing 1 to 12 carbon atoms; a cycloalkyl radical, or an aralkyl radical containing 6 to 12 carbon atoms; and
   $R_2$ represents a linear or branched alkyl radical containing 1 to 4 carbon atoms.

10. A process according to claim 9, wherein
   $R_1$ represents a linear or branched alkyl radical containing 1 to 8 carbon atoms;
   a cycloalkyl radical containing 6 carbon atoms or an aralkyl radical containing 7 or 8 carbon atoms; and
   $R_2$ represents a linear or branched alkyl radical containing 1 to 2 carbon atoms.

11. A process according to claim 7, wherein the alkylsalicylic ester has general formula (I), wherein $R_1$ is methyl, ethyl, n-propyl, isopropyl, butyl, isobutyl, sec-butyl, tert-butyl, amyl, isoamyl, n-hexyl 2-ethylhexyl, a cyclohexyl radical; a benzyl radical; or a β-phenylethyl radical, and $R_2$ is methyl or ethyl radical.

12. A process according to claim 7, wherein the alkylsalicylic acid ester is:
methyl 2-hydroxy-3-methyl-benzoate;
ethyl 2-hydroxy-3-methyl-benzoate;
isopropyl 2-hydroxy-3-methyl-benzoate;
n-propyl 2-hydroxy-3-methyl-benzoate;
n-butyl 2-hydroxy-3-methyl-benzoate;
isobutyl 2-hydroxy-3-methyl-benzoate;
amyl 2-hydroxy-3-methyl-benzoate;
isoamyl 2-hydroxy-3-methyl-benzoate;
n-hexyl 2-hydroxy-3-methyl-benzoate;
2-ethylhexyl 2-hydroxy-3-methyl-benzoate;
cyclohexyl 2-hydroxy-3-methyl-benzoate;
benzyl 2-hydroxy-3-methyl-benzoate;
β-phenylethyl 2-hydroxy-3-methyl-benzoate;
methyl 2-hydroxy-4-methyl-benzoate;
ethyl 2-hydroxy-4-methyl-benzoate;
isopropyl 2-hydroxy-4-methyl-benzoate;
n-propyl 2-hydroxy-4-methyl-benzoate;
n-butyl 2-hydroxy-4-methyl-benzoate;
isobutyl 2-hydroxy-4-methyl-benzoate;
amyl 2-hydroxy-4-methyl-benzoate;
isoamyl 2-hydroxy-4-methyl-benzoate;
n-hexyl 2-hydroxy-4-methyl-benzoate;
2-ethylhexyl 2-hydroxy-4-methyl-benzoate;
cyclohexyl 2-hydroxy-4-methyl-benzoate;
benzyl 2-hydroxy-4-methyl-benzoate;
β-phenylethyl 2-hydroxy-4-methyl-benzoate;
methyl 2-hydroxy-5-methyl-benzoate;
ethyl 2-hydroxy-5-methyl-benzoate;
isopropyl 2-hydroxy-5-methyl-benzoate;
n-propyl 2-hydroxy-5-methyl-benzoate;
n-butyl 2-hydroxy-5-methyl-benzoate;
isobutyl 2-hydroxy-5-methyl-benzoate;
amyl 2-hydroxy-5-methyl-benzoate;
isoamyl 2-hydroxy-5-methyl-benzoate;
n-hexyl 2-hydroxy-5-methyl-benzoate;
2-ethylhexyl 2-hydroxy-5-methyl-benzoate;
cyclohexyl 2-hydroxy-5-methyl-benzoate;
benzyl 2-hydroxy-5-methyl-benzoate; or
β-phenylethyl 2-hydroxy-5-methyl-benzoate.

13. A perfumed article in the form of a perfume, eau de toilette, aftershave lotion, soap, bath gel, shower gel, deodorising product, antiperspirant product, shampoo, haircare product, talc, cosmetic powder, air freshener, cleaning product, detergent composition or a fabric softener comprising a perfuming composition as defined in claim 7.

14. A method of using alkylsalicylic acid esters as a perfuming ingredient of a product, comprising the step of adding 0.01% and 90% of said alkylsalicylic acid esters by weight to said product, wherein the alkylsalicylic acid ester has general formula (I):

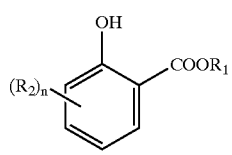

(I)

wherein:
   n is a number equal to 1 or 2;
   $R_1$ represents a hydrocarbon radical, containing 1 to 40 carbon atoms; or a saturated or unsaturated, monocyclic or polycyclic, carbocyclic or heterocyclic radical; and $R_2$ represents an aliphatic optionally saturated radical having 1 to 4 carbon atoms.

15. A method according to claim 14, wherein
$R_1$ represents a linear or branched, saturated or unsaturated, aliphatic, acyclic radical; and
$R_2$ represents an aliphatic saturated radical with less than 4 carbon atoms.

16. A method according to claim 14, wherein the alkyl-salicylic acid ester has general formula (Ia):

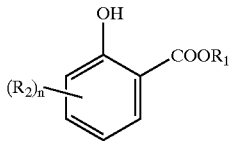

(Ia)

wherein:
n is a number equal to 1 or 2;
$R_1$ represents a linear or branched alkyl radical containing 1 to 12 carbon atoms; a cycloalkyl radical, or an aralkyl radical containing 6 to 12 carbon atom; and
$R_2$ represents a linear or branched alkyl radical containing 1 to 4 carbon atoms.

17. A method according to claim 16, wherein
$R_1$ represents a linear or branched alkyl radical containing 1 to 8 carbon atoms;
a cycloalkyl radical containing 6 carbon atoms; or an aralkyl radical containing 7 or 8 carbon atoms; and
$R_2$ represents a linear or branched alkyl radical containing 1 to 2 carbon atoms.

18. A method according to claim 14, wherein the alkyl-salicylic acid ester has general formula (I) in which $R_1$ is methyl, ethyl, n-propyl, isopropyl, butyl, isobutyl, sec-butyl, tert-butyl, amyl, isoamyl, n-hexyl 2-ethylhexyl; a cyclohexyl radical; a benzyl radical, or a β-phenylethyl radical, and $R_2$ represents a methyl or ethyl radical.

19. A method according to claim 14, wherein the alkyl-salicylic acid ester is:

methyl 2-hydroxy-3-methyl-benzoate;
ethyl 2-hydroxy-3-methyl-benzoate;
isopropyl 2-hydroxy-3-methyl-benzoate;
n-propyl 2-hydroxy-3-methyl-benzoate;
n-butyl 2-hydroxy-3-methyl-benzoate;
isobutyl 2-hydroxy-3-methyl-benzoate;
amyl 2-hydroxy-3-methyl-benzoate;
isoamyl 2-hydroxy-3-methyl-benzoate;
n-hexyl 2-hydroxy-3-methyl-benzoate;
2-ethylhexyl 2-hydroxy-3-methyl-benzoate;
cyclohexyl 2-hydroxy-3-methyl-benzoate;
benzyl 2-hydroxy-3-methyl-benzoate;
β-phenylethyl 2-hydroxy-3-methyl-benzoate;
methyl 2-hydroxy-4-methyl-benzoate;
ethyl 2-hydroxy-4-methyl-benzoate;
isopropyl 2-hydroxy-4-methyl-benzoate;
n-propyl 2-hydroxy-4-methyl-benzoate;
n-butyl 2-hydroxy-4-methyl-benzoate;
isobutyl 2-hydroxy-4-methyl-benzoate;
amyl 2-hydroxy-4-methyl-benzoate;
isoamyl 2-hydroxy-4-methyl-benzoate;
n-hexyl 2-hydroxy-4-methyl-benzoate;
2-ethylhexyl 2-hydroxy-4-methyl-benzoate;
cyclohexyl 2-hydroxy-4-methyl-benzoate;
benzyl 2-hydroxy-4-methyl-benzoate;
β-phenylethyl 2-hydroxy-4-methyl-benzoate;
methyl 2-hydroxy-5-methyl-benzoate;
ethyl 2-hydroxy-5-methyl-benzoate;
isopropyl 2-hydroxy-5-methyl-benzoate;
n-propyl 2-hydroxy-5-methyl-benzoate;
n-butyl 2-hydroxy-5-methyl-benzoate;
isobutyl 2-hydroxy-5-methyl-benzoate;
amyl 2-hydroxy-5-methyl-benzoate;
isoamyl 2-hydroxy-5-methyl-benzoate;
n-hexyl 2-hydroxy-5-methyl-benzoate;
2-ethylhexyl 2-hydroxy-5-methyl-benzoate;
cyclohexyl 2-hydroxy-5-methyl-benzoate;
benzyl 2-hydroxy-5-methyl-benzoate; or
β-phenylethyl 2-hydroxy-5-methyl-benzoate.

20. A process according to claim 1, wherein between 0.01% and 90% of said alkylsalicylic acid ester is added.

21. A perfuming composition according to claim 7, comprising between 0.01% and 90% of said alkylsalicylic acid ester.

22. A process according to claim 1 for the production of a perfuming composition, a perfumed product or a substance for perfumery, having a sensual flowery scent, comprising the step of adding an effective perfuming amount of ethyl 2-hydroxy-4-methylbenzoate.

23. A process according to claim 1 for the production of a perfuming composition, a perfumed product or a substance for perfumery, having a phenolic aniseed scent, comprising the step of adding an effective perfuming amount of methyl 2-hydroxy-4-methylbenzoate.

24. A process according to claim 1 for the production of a perfuming composition, a perfumed product or a substance for perfumery, having a saffron violet scent, comprising the step of adding an effective perfuming amount of methyl 2-hydroxy-5-methylbenzoate.

* * * * *